US00PP24681P3

(12) United States Plant Patent
Deng et al.

(10) Patent No.: US PP24,681 P3
(45) Date of Patent: Jul. 22, 2014

(54) ***CALADIUM* PLANT NAMED 'UF-85-5'**

(50) Latin Name: *Caladium hortulanum*
Varietal Denomination: UF-85-5

(75) Inventors: Zhanao Deng, Riverview, FL (US); Brent K. Harbaugh, Bradenton, FL (US)

(73) Assignee: Florida Foundation Speed Producers, Inc., Marianna, FL (US)

( * ) Notice: Subject to any disclaimer, the term of this patent is extended or adjusted under 35 U.S.C. 154(b) by 47 days.

(21) Appl. No.: 13/507,998

(22) Filed: Aug. 10, 2012

(65) Prior Publication Data

US 2014/0047599 P1 Feb. 13, 2014

(51) Int. Cl.
*A01H 5/00* (2006.01)

(52) U.S. Cl.
USPC ..... Plt./373

(58) Field of Classification Search
USPC ..... Plt./373
See application file for complete search history.

(56) References Cited

U.S. PATENT DOCUMENTS

PP20,446 P2 11/2009 Deng et al.
PP20,792 P3 2/2010 Deng et al.

OTHER PUBLICATIONS

U.S. Appl. No. 13/508,000, Aug. 10, 2013, Deng et al.
U.S. Appl. No. 13/507,999, Aug. 10, 2013, Deng et al.
Bell et al., "Survey of caladium tuber producers for acreage of cultivars grown," *Proc. Fla. State Hort. Soc.* 111:32-34, 1998.
Deng et al., "Summer Rose, a fancy-leaved caladium for containers and landscapes," *HortScience* 41:468-470, 2006.
Deng et al., "2003 survey of the Florida caladium tuber production industry," *Univ. Fla., Inst. Food Agric. Sci. EDIS Publication ENH 1007* <http://edis.ifas.ufl.edu/EP258>, 2005.
Geraldson et al., "Combination of high analysis fertilizers, plastic mulch and fumigation for tomato production on old agricultural land," *Proc. Soil and Crop Sci. Fla.* 25:18-24, 1965.
Wilfret, "Florida Fantasy, a multicolored caladium for containers," *Circular S—Univ. Fla., Inst. Food Agric. Sci.* 381, 1991.

*Primary Examiner* — Kent L Bell
(74) *Attorney, Agent, or Firm* — Dentons US LLP

(57) ABSTRACT

A new and distinct cultivar of *Caladium* plant named 'UF-85-5' is disclosed. 'UF-85-5' is characterized by its fancy leaves with a white/green leaf face and red spots, and it has been demonstrated to sprout early, produce attractive pot plants when tubers are forced in containers, and it possess exceptional sunburn tolerance.

4 Drawing Sheets

ACKNOWLEDGEMENT OF FEDERAL RESEARCH SUPPORT

This invention was made with government support under FLA-BRA-04162 awarded by the Cooperative State Research, Education, and Extension Service, USDA. The government has certain rights in the invention.

Latin name of the genus and species of the plant claimed: *Caladium hortulanum.*

Variety denomination: 'UF-85-5'.

BACKGROUND OF THE INVENTION

*Caladiums [Caladium hortulanum* Birdsey, Araceae Juss.] are ornamental aroids valued for their bright colorful leaves. They are propagated through tubers and tuber divisions. Many existing commercial *Caladium* cultivars cannot produce tubers stably or adequately for profitable commercial production. In other cases, sunburn tolerance or pot performance may not be satisfactory for commercial acceptance.

'UF-85-5' originated from a planned cross between 'UF-607' (female parent) and 'Florida Fantasy' (male parent) that was made in 2000. 'UF-607' was chosen from progeny of 'Aaron' and a breeding line, UF-FCT, that resulted from a cross between 'Fire Chief' and 'Torchy'. 'UF-607' was released as 'Summer Rose' in 2005 (Deng and Harbaugh, *HortScience,* 41:468-470, 2006, U.S. Plant Pat. No. 20,446). 'Florida Fantasy' (unpatented) was a progeny of a cross between '*Candidum* Junior' and 'Red Frill' (Wilfret, *Univ. Fla., Inst. Food Agric. Sci., Circular*, S-381, Gainesville, Fla., 1991). The ancestry of 'Aaron', '*Candidum* Junior', 'Fire Chief', 'Red Frill', and 'Torchy' is unknown. 'UF-85-5' was selected in 2001. Asexual propagation by tubers and tuber division, and evaluations in field and pot studies in Bradenton, Fla. between 2002 and 2005 and in Wimauma, Fla. since 2005 have shown that the unique features of 'UF-85-5' are stable and 'UF-85-5' reproduces true to type in successive generations of asexual propagation.

Plant Breeder's Rights for this cultivar have not been applied for. 'UF-85-5' has not been made publicly available more than one year prior to the filing of this application.

SUMMARY OF THE INVENTION

'UF-85-5' is a fancy-leaved *Caladium* uniquely characterized with a white/green leaf face and red spots.

Compared to female parent 'UF-607' ('Summer Rose', U.S. Plant Pat. No. 20,446), the leaves of 'UF-85-5' are green-veined, while the leaves of 'UF-607' are pink/red-veined. In addition, the leaves of 'UF-85-5' express a primarily white/green face and are spotted, while leaves of 'UF-607' ('Summer Rose') express a primarily pink face and are non-spotted.

Compared to male parent 'Florida Fantasy' (unpatented), leaves of 'UF-85-5' are green-veined and spotted, while leaves of 'Florida Fantasy' are red-veined and non-spotted.

Plants of the new *Caladium* can also be compared to plants of the cultivar 'Marie Moir' (unpatented). In side-by-side comparisons conducted in the greenhouse in Wimauma, Fla., plants of 'UF-85-5' differ primarily from plants of 'Marie Moir' in leaf development and petiole color. Plants of 'UF-85-5' produce at least twice as many leaves as plants of 'Marie Moir' when grown in containers or in ground beds (Tables 2 and 3). Leaf petioles of 'UF-85-5' are green, whereas leaf petioles of 'Maire Moir' are darker brown.

Plants of 'UF-85-5' can also be compared to plants of the cultivar 'Cranberry Star' *Caladium* (U.S. Plant Pat. No. 20,792) in leaf color, color of spots, and sunburn tolerance. In side-by-side comparisons, plants of 'UF-85-5' express a white/green leaf face, red spots, and, excellent sunburn tolerance, while plants of 'Cranberry Star' express a more pure-white leaf face with fewer green veins, burgundy to purple spots, and susceptibility to sunburn.

BRIEF DESCRIPTION OF THE DRAWINGS

'UF-85-5' has not been observed under all possible environmental conditions. Its phenotype may vary somewhat with variations in the environment such as light intensity and temperature, without, however, any variance in genotype. The accompanying photographs show the colors as true as it is reasonably possible to obtain in colored reproductions of this type. Colors in the photographs may differ slightly from the color values cited in the detailed botanical description which accurately describe the colors of the new *Caladium*.

DETAILED BOTANICAL DESCRIPTION

Figure 1:
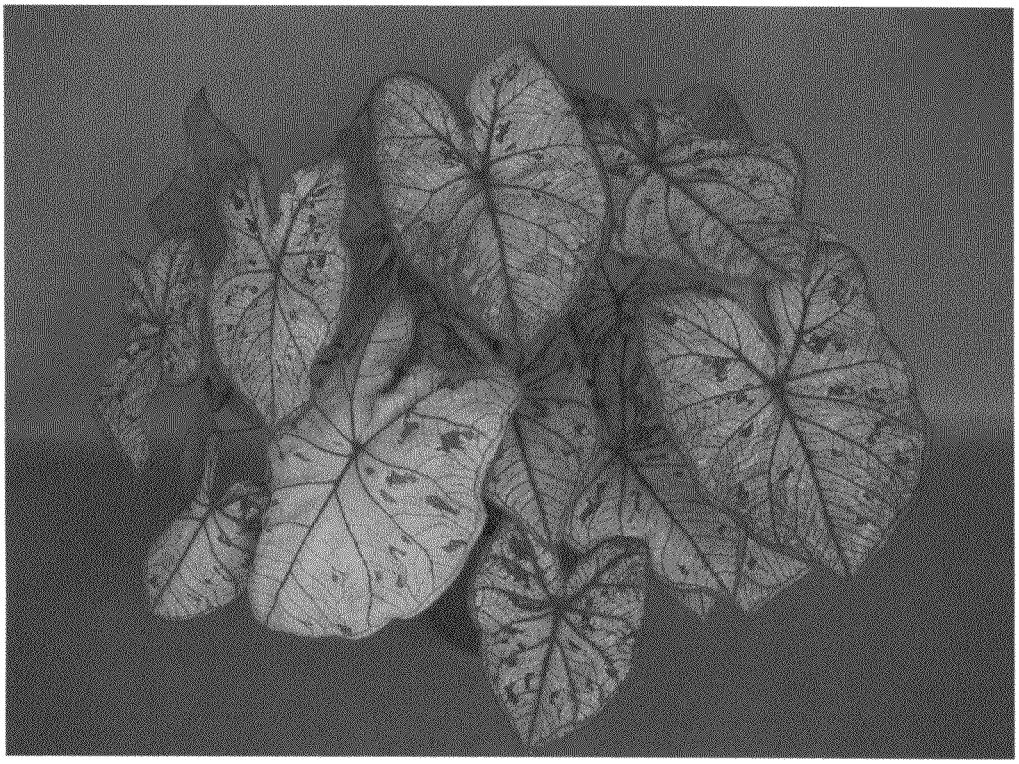
FIG. 1: Shows a side perspective view of a typical plant of 'UF-85-5' grown in a container in a shadehouse in Wimauma, Fla.
Figure 2:
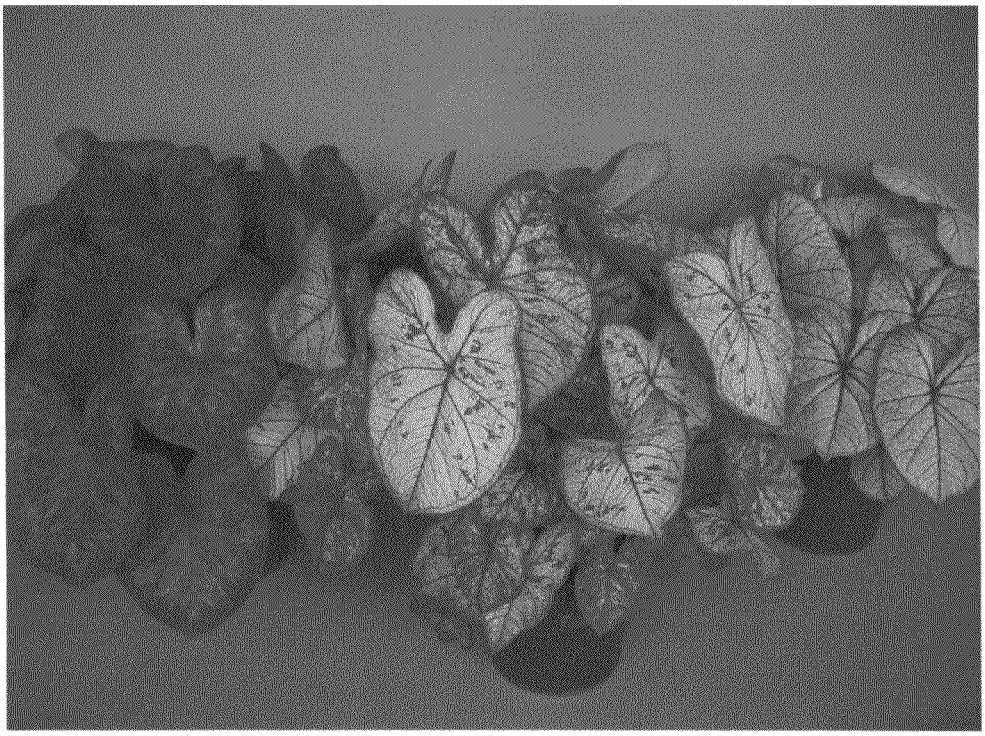
FIG. 2: Shows a side perspective view of typical plants of female parent 'Summer Rose' (left), 'UF-85-5' (center), and male parent 'Florida Fantasy' (right) grown in containers in a shadehouse in Wimauma, Fla.
Figure 3:
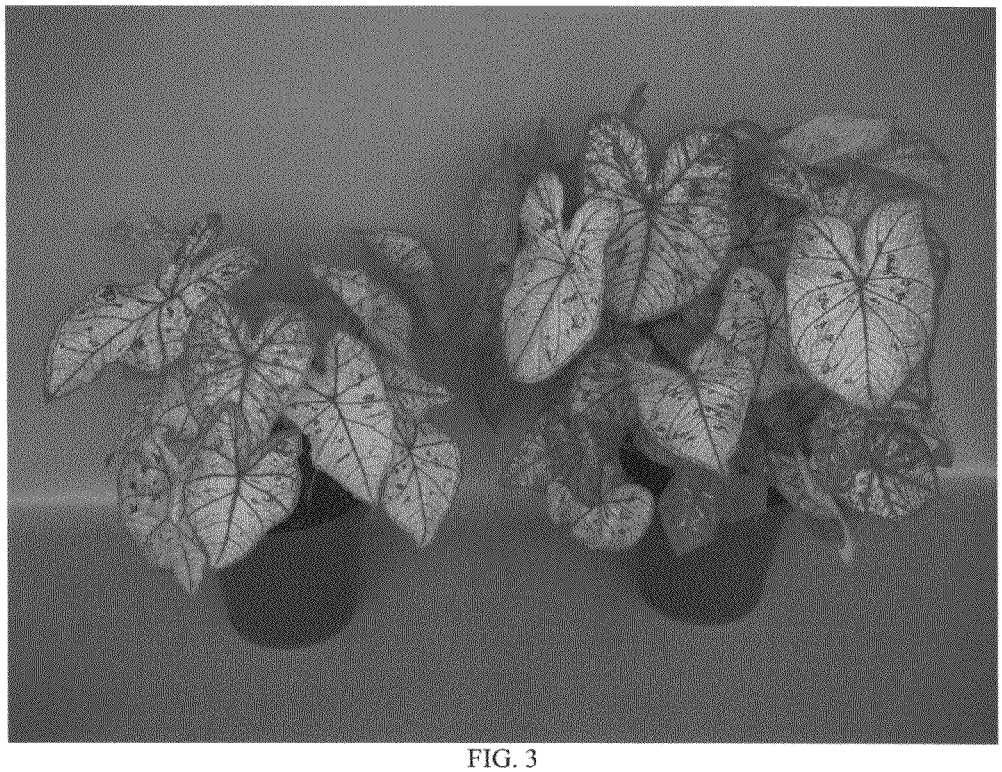
FIG. 3: Shows a side perspective view of typical plants of closest counterpart 'Marie Moir' (left) and 'UF-85-5' (right) grown in a shadehouse in Wimauma, Fla.
Figure 4:
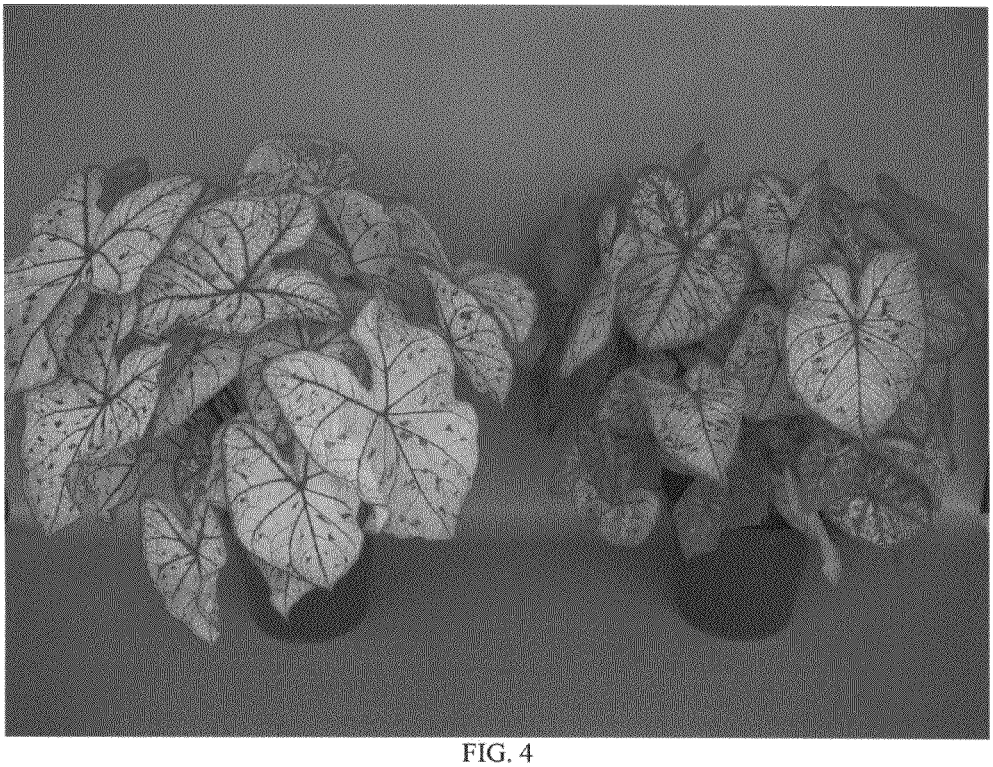
FIG. 4: Shows a side perspective view of typical plants of 'Cranberry Star' (left) and 'UF-85-5' (right) grown in a shadehouse in Wimauma, Fla.

In the following description, color references are made to The Royal Horticultural Society Colour Chart, 1986 Edition, except where general terms of ordinary dictionary significance are used. The aforementioned photographs and following observations and measurements describe plants grown in 20.3-cm containers in Wimauma, Fla. during the summer in a polypropylene-covered shadehouse, and plants grown in ground beds in Wimauma, Fla. during the late summer in an outdoor nursery. All plants were grown under conditions and practices which approximate those generally used in commercial *Caladium* production.

During the production of the plants, day temperatures ranged from about 23.8-34.4° C., night temperatures ranged from about 20.5-23.8° C., and light levels were about 944 (shadehouse) or 9744 foot-candles (outdoor nursery). Plants grown in the shadehouse were about eight weeks from planting tubers when the photographs and detailed description were taken. Plants grown in the outdoor nursery were about fourteen weeks from planting tuber pieces when the photographs and detailed description were taken.

Phenotypic description of *Caladium hortulanum* variety 'UF-85-5': Common name: *Caladium.*

Tuber description:

*Color.*—Epidermis: brown (RHS 200B to 200D). Interior: yellow (RHS 13B).

Root description: Dense, thick and white fleshy roots.

Plant description:

*Plant type.*—Herbaceous perennial.

*Plant/growth habit.*—Compact and upright, dense growth habit; suitable for 10-25-cm containers. Leaf petioles arising from tubers; petioles mostly upright and curving outwardly with development.

*Plant height, from soil level to top of leaf plane, shadehouse-grown plants.*—~19.5-23 cm.

*Plant height, from soil level to top of inflorescences, shadehouse-grown plants.*—~37 cm.

*Plant diameter or spread, shadehouse-grown plant.*—~42.5 cm×35.5 cm.

*Plant height, from soil level to top of leaf plane, outdoor nursery-grown plants.*—~24-37 cm.

*Plant height, from soil level to top of inflorescences, outdoor nursery-grown plants.*—No inflorescences were observed on plants grown in the outdoor nursery.

*Plant diameter or spread, outdoor nursery-grown plants.*—~51 cm×44 cm.

Foliage description (shadehouse-grown and outside grown):

*Length of leaf blades, shadehouse-grown plants.*—~12.5-18 cm.

*Width of leaf blades, shadehouse-grown plants (flattened).*—~9-11 cm.

*Length of leaf blades, outdoor nursery-grown plants.*—~17-23 cm.

*Width of leaf blades, outdoor nursery-grown plants (flattened).*—~11-15 cm.

*Shape.*—Peltate, ovate.

*Apex.*—Acuminate to acute.

*Base.*—Cordate. Margin: Entire. Texture, upper surface: Smooth, glabrous. Texture, lower surface: Smooth, glabrous, glaucous.

*Venation pattern.*—Palmate-pinnate.

*Color, shadehouse-grown plants.*—Developing and fully expanded leaves. upper surface: Center: Green-white (RHS 157D) with green (RHS 137A) and medium-sized blotches of red (RHS 46A). Border and margins: Green (RHS 137C). Basal notch: Purple (RHS 79B). Venation: Midrib and primary veins: Green (RHS 137A). Developing and fully expanded leaves. Lower surface: Center: Yellow-green (RHS 145D) and greyed-green veins (RHS 191A) with varying sizes of blotches greyed-purple (RHS 184C). Border and margins: Yellow-green (RHS 145D) with greyed-green veins (RHS 191A). Venation: Midrib and primary veins: Greyed-green (RHS 193C) and darken to greyed-green (RHS 193A) by the tip of the leaf. Netted veins are greyed-green (RHS 191A) throughout the leaf.

*Color, outdoor nursery-grown plants.*—Developing leaves, upper surface: Center: White (RHS 155B) and veins of green (RHS 137A) with blotches of red (RHS 53B). Border and margins: Green (RHS 137A). Venation: Midrib and primary veins: All veins green (RHS 137A). Developing leaves, lower surface: Center: Green-white (RHS 157B and 157C) with veins of greyed-green (RHS 191A) and blotches of greyed-purple (RHS 184D). Border and margins: Greyed-green (RHS 191A). Venation: Midrib and primary veins: Midrib: Green-white (RHS 157A); Primary: Greyed-green (RHS 191B) and netted veins greyed-green (RHS 191A). Fully expanded leaves, upper surface: Center: White (RHS 155B) and veins of green (RHS 137A) with blotches of red (RHS 53A). Border and margins: Green (RHS 137A). Venation: Midrib and primary veins: All veins are green (RHS 137A) with basal notch spot of greyed-purple (RHS 187A). Fully expanded leaves, lower surface: Center: Green-white (RHS 157B and 157C) and veins of greyed-green (RHS 191A) with several botches of greyed-purple (RHS 184B). Border and margins: Greyed-green (RHS 191A). Venation: Midrib: Grey-white (RHS 155A) primary veins: Greyed-green (RHS 191B) and netted veins greyed-green (RHS 191A).

*Petiole*.—Aspect: Mostly erect, curving outwardly with development. Length, shadehouse-grown plants: ~16-23 cm. Diameter, distal, shadehouse-grown plants: ~3 mm. Diameter, proximal, shadehouse-grown plants: ~6 mm. Length, outdoor nursery-grown plants: ~23-33 cm. Diameter, distal, outdoor nursery-grown plants: ~3.7 mm. Diameter, proximal, outdoor nursery-grown plants: ~7.3 mm. Strength: Strong; flexible. Color, shadehouse-grown plants: 2 unique colors: Yellow-green (RHS 144C) with few streaks of yellow-green (RHS 147A) or yellow-green (RHS 145D) with long streaks and blotches of brown (RHS 200B). Color, proximal, outdoor nursery-grown plants: Yellow-green (RHS 147A) with long streaks of green-white (RHS 157D). Wing length, shadehouse-grown plants: ~4-5 cm. Wing diameter, shadehouse-grown plants: ~4.5-6 mm. Wing length, outdoor nursery-grown plants: ~7 cm. Wing diameter, outdoor nursery-grown plants: ~6.3 mm. Wing color, shadehouse-grown plants: Orange-white (RHS 159C) with some streaks of brown (RHS 200C). Wing color, outdoor nursery-grown plants: Green-white (RHS 157D) with streaks of yellow-green (RHS 147A).

Inflorescence description: Inflorescences only observed on shadehouse-grown plants.

*Inflorescence arrangement*.—Upright hooded spathes surrounding a columnar spadix borne on a tall upright scape. Spadix with sessile, simple female and male flowers separated into two zones. Female flowers arranged on the lower one-third of the spadix; male flowers arranged on the upper two-thirds of the spadix. Sterile flowers develop between female and male flower zones; near this area, the spathe constricts surrounding the female flowers.

*Fragrance*.—None detected.

*Natural flowering season/longevity*.—Plants of the new *Caladium* typically flower during the spring or early summer in central Florida. Inflorescences last about three days before fading; inflorescences persistent.

Spathe:

*Length*.—~11.5 cm.
*Width, distal*.—~2.5 cm.
*Width, proximal*.—~2 cm.
*Shape*.—Ovate to obovate.
*Apex*.—Acute to acuminate.
*Base*.—Tapering.
*Margin*.—Entire.
*Texture, upper and lower surfaces*.—Smooth, glabrous.
*Color*.—Front surface: Upper two-thirds: White (RHS 155B), with color becoming closer to more brown than 199D with development. Lower one-third: Green (RHS 143C). Rear surface: Upper two-thirds: White (RHS 155D) with both outer edges of white (RHS 155A). Lower one-third: Yellow-green (RHS 144D) with many streaks of yellow-green (RHS 144B).

Spadix:

*Length, entire spadix*.—~6.7 cm.
*Length, male flower zone*.—~3.5 cm.
*Length, sterile flower zone*.—~2 cm.
*Length, female flower zone*.—~1.3 cm.
*Diameter, male flower zone*.—~8 mm.
*Diameter, sterile flower zone*.—7 mm.
*Diameter, female flower zone*.—~1 cm.
*Shape*.—Spindle-shaped to columnar.
*Apex*.—Obtuse.
*Base*.—Obtuse.
*Aspect*.—Upright.
*Color, mature, male zone*.—Yellow-white (RHS 158A).
*Color, mature, sterie zone*.—White (RHS 155B).
*Color, mature, female zone*.—Yellow (RHS 11B).

Male flowers:

*Quantity per spadix*.—~85.
*Shape*.—Obovate.
*Height*.—~2 mm.
*Diameter*.—~3 mm.

Female flowers:

*Quantity per spadix*.—~84.
*Shape*.—Obovate.
*Height*.—~2 mm.
*Diameter*.—~2 mm.

Scape:

*Length*.—~25 cm.
*Diameter*.—~5 mm.
*Strength*.—Sturdy; flexible.
*Aspect*.—Erect.
*Texture*.—Smooth, glabrous; glaucous.
*Color*.—Mainly yellow-green (RHS 145D) with small blotches of greyed-green (RHS 191A). Just below spathe, yellow-green (RHS 144A).

Disease and insect resistance: Disease and insect resistance is typical of the species.

Performance:

'UF-85-5' was evaluated for tuber production and plant performance under field conditions in Wimauma, Fla. in 2005 and 2006. The soil was an EauGallie fine sand with about 1% organic matter and a pH of 6.2. Plants were grown in a plastic-mulched raised-bed system maintaining a constant water table with seepage irrigation (Geraldson et al., *Proc. Soil and Crop Sci. Soc. Fla.* 25:18-24, 1965). In 2005, ground beds were fumigated on February 25 (6 weeks before planting), with a mixture of 67% methyl bromide and 33% chloropicrin (by volume) at the rate of 392 $kg \cdot ha^{-1}$, and in 2006, the beds were fumigated on March 10, 10 days before planting, with the same fumigant mixture, but at the rate of 196 $kg \cdot ha^{-1}$. Ground beds were 91 cm wide and 20 cm high. *Caladium* seed pieces (cut tuber propagules, about 2.5 cm) were planted 15 cm apart in three rows. Osmocote 18N-2.6P-10K 8-9 month controlled release fertilizer (Scotts Co., Marysville, Ohio) was applied to the bed surface when shoot tips emerged from the soil with nitrogen at 336 $kg \cdot ha^{-1}$.

Field plots were organized in three randomized complete blocks, and each plot was 1.25 $m^2$ with 30 plants. In 2005, seed tuber pieces were planted in April and tubers were harvested in November; in 2006, seed pieces were planted in April and tubers were harvested in December. Each year, dried tubers were weighed and counted per plot, and then graded by maximum diameter: No. 2 (2.5-3.8 cm), No. 1 (3.8-6.4 cm), Jumbo (6.4-8.9 cm), Mammoth (8.9-11.4 cm), and Super Mammoth (>11.4 cm). The production index, an indicator of economic value of the harvested tubers, was calculated as: N (No. 2)+2N (No. 1)+4N (Jumbo)+6N (Mammoth)+8N (Super Mammoth); where N=number of tubers in each grade. An analysis of variance was conducted using the GLM procedure in the SAS program (SAS Institute, 2009) to compare the performance of 'UF-85-5' to that of '*Candidum*', 'Marie Moir', and 'Miss Muffet'. '*Candidum*' was used for comparison, as it has been the No. 1 or 2 best-selling cultivar (Bell et al., *Proc. Fla. State Hort. Soc.* 111:32-34, 1998; Deng et al., *Univ. Fla., Inst. Food Agric. Sci., EDIS Publication #ENH*1007, Gainesville, Fla., 2008) and shares a similar coloration pattern to 'UF-85-5', except for not having colored spots on the leaf blades. 'Marie Moir' was the closest to 'UF-85-5' in leaf coloration among commercial cultivars. 'Miss Muffet' was used because it is a dwarf spotted-leaf cultivar.

'UF-85-5' was significantly more productive than '*Candidum*' and 'Miss Muffet' in both the 2005 and 2006 growing seasons. Its average tuber weight was 115% (2005) and 83% (2006) greater than '*Candidum*' and 75% (2005) and 103% (2006) greater than 'Miss Muffet'; its production index was 66% (2005) and 53% (2006) higher than '*Candidum*' and 49% (2005) and 65% (2006) higher than 'Miss Muffet'; and its number of marketable tubers was 50% (2005) and 44% (2006) larger than 'Candidum' and 36% (2005) and 28% (2006) larger than 'Miss Muffet' (Table 1). 'UF-85-5' had consistent tuber weight, number of marketable tubers, and production index from 2005 to 2006, while 'Marie Moir' had poor consistency between growing seasons in tuber production. 'Marie Moir' yielded similarly well compared to 'UF-85-5' in 2005, but yielded poorly compared to 'UF-85-5' in 2006—approximately 33% less than 'UF-85-5's tuber weight and production index, and only about 50% of 'UF-85-5's number of marketable tubers.

TABLE 1

Tuber weight, production index, number, and grade distribution of five *Caladium* cultivars (2005 and 2006). Values presented are means of three replications with 30 propagules planted in a plot.

| | Tuber | | | Tuber distribution (%)[z] | |
|---|---|---|---|---|---|
| Cultivar | Weight (kg) | Production index[y] | Marketable (no.) | Super mammoth | Mammoth |
| | | | Year 2005 | | |
| 'UF-85-5' | 5.6 | 171 | 50.6 | 6.3 | 13.3 |
| 'Candidum' | 2.6 | 103 | 33.7 | 0 | 4.0 |
| 'Marie Moir' | 5.0 | 159 | 46.2 | 2.3 | 16.7 |
| 'Miss Muffet' | 3.2 | 115 | 37.3 | 0 | 10.3 |
| | | | Year 2006 | | |
| 'UF-85-5' | 5.5 | 175 | 49.8 | 7.3 | 16.0 |
| 'Candidum' | 3.0 | 114 | 34.6 | 2.3 | 11.7 |
| 'Marie Moir' | 1.5 | 58 | 29.9 | 2.3 | 0 |
| 'Miss Muffet' | 2.7 | 106 | 38.7 | 0 | 10.0 |

TABLE 1-continued

Tuber weight, production index, number, and grade distribution of five *Caladium* cultivars (2005 and 2006). Values presented are means of three replications with 30 propagules planted in a plot.

| | Tuber distribution (%)[z] | | |
|---|---|---|---|
| Cultivar | Jumbo | No. 1 | No. 2 |
| | | Year 2005 | |
| 'UF-85-5' | 30.0 | 39.3 | 11.3 |
| 'Candidum' | 47.7 | 42.3 | 6.0 |
| 'Marie Moir' | 37.3 | 35.0 | 8.7 |
| 'Miss Muffet' | 40.0 | 40.0 | 10.3 |
| | | Year 2006 | |
| 'UF-85-5' | 30.7 | 29.7 | 16.3 |
| 'Candidum' | 38.7 | 37.7 | 9.3 |
| 'Marie Moir' | 11.3 | 43.7 | 43.0 |
| 'Miss Muffet' | 28.3 | 42.7 | 19.0 |

[z]Tubers graded by maximum diameter; No. 2 (2.5-3.8 cm), No. 1 (3.8-6.4 cm), Jumbo (6.4-8.9 cm), Mammoth (8.9-11.4 cm), and Super Mammoth (>11.4 cm). Tuber distribution data (%) were transformed using the formula arcsine [square root (percentage/100)] before analysis of variance and mean separation.
[y]The production index is an indicator of economic value of the crop harvested and is calculated as: N (No. 2) + 2N (No. 1) + 4N (Jumbo) + 6N (Mammoth) + 8N (Super Mammoth), where N = number of tubers in each grade.

Landscape performance of cultivars grown under full-sun conditions was evaluated in 2005 and 2006 under the same conditions used for evaluating tuber production. 'Cranberry Star' was also included with '*Candidum*', 'Marie Moir', and 'Miss Muffet' for comparison to 'UF-85-5' in this test. The overall plant performance was rated multiple times (June, July, and August) in each growing season, on a scale of 1 to 5, with 1 being very poor (few leaves and lack of vigor), and 5 being excellent (full plants, numerous leaves, and bright color display). Similarly, leaf sunburn tolerance was also evaluated multiple times in each growing season on a scale of 1 to 5, with 1 being very susceptible to sunburns and showing numerous sun-damaged areas or holes on leaves and 5 being resistant to sunburns and not showing any sun-damaged areas. Approximately 4 months after planting, plant height, number of leaves, and foliar characteristics were measured.

Plants of 'UF-85-5' and 'Cranberry Star' were 9-13 cm taller and developed significantly more (~100%) leaves than '*Candidum*' and 'Marie Moir' (Table 2). Leaf sizes were similar among all cultivars tested, except for 'Miss Muffet', a known dwarf cultivar that was about half the size of other cultivars. 'UF-85-5' plants performed well in the landscape, with performance ratings between 3.6 and 4.8, similar to 'Cranberry Star', but significantly higher than those of '*Candidum*' (1.7-3.1), 'Marie Moir' (1.4-3.3) and 'Miss Muffet' (1.5-2.4). 'UF-85-5' received the highest sunburn tolerance ratings in all the evaluations in each growing season, indicating better or significantly better sun tolerance in this cultivar in comparison to '*Candidum*', 'Marie Moir', and 'Miss Muffet', and potential for use in sunny locations in the landscape. While 'UF-85-5' showed a high level of similarity to 'Cranberry Star', a recent release, in plant height, leaf number and leaf size, 'Cranberry Star' was very susceptible to leaf damage in full sun and thus limited to use in shady locations.

TABLE 2

Plant characteristics, performance, and sun tolerance from planting 2.5-cm *Caladium* tuber propagules in ground beds in full sun (2005 and 2006). Values presented for plant height, leaf number, length, and width are means of three replications with three plants measured per plot per year, while performance and sun burn tolerance ratings are means of three replications based on whole plot evaluation.

| Cultivar | Plant height[z] (cm) | Leaves[z] (no.) | Leaf length[z] (cm) | Leaf width[z] (cm) |
|---|---|---|---|---|
| 'UF-85-5' | 41.9 | 27.3 | 24.9 | 15.0 |
| 'Candidum' | 31.5 | 14.6 | 23.8 | 15.4 |
| 'Cranberry Star' | 37.0 | 24.9 | 24.8 | 15.8 |
| 'Marie Moir' | 28.1 | 13.9 | 24.5 | 15.4 |
| 'Miss Muffet' | 18.1 | 16.3 | 16.8 | 10.9 |

| | Performance rating[y] | | | Sun tolerance rating[x] | | |
|---|---|---|---|---|---|---|
| Cultivar | June | July | August | June | July | August |
| 'UF-85-5' | 3.6 | 4.3 | 4.8 | 3.5 | 4.5 | 4.8 |
| 'Candidum' | 1.7 | 1.5 | 3.1 | 2.7 | 2.6 | 3.6 |
| 'Cranberry Star' | 2.6 | 4.0 | 4.6 | 1.8 | 3.6 | 3.0 |
| 'Marie Moir' | 1.4 | 1.6 | 3.3 | 1.9 | 4.2 | 4.1 |
| 'Miss Muffet' | 1.5 | 1.3 | 2.4 | 3.3 | 4.4 | 4.2 |

[z]Data were taken over two growing seasons (2005 and 2006), approximately 4 months (August 2005 and 2006) after tubers were planted in April each year.
[y]Plants were rated on a scale of 1 to 5, with 1 being very poor, 3 being fair and acceptable, and 5 being excellent in plant vigor, fullness, and color display, in June, July, and August in 2005 and 2006, respectively.
[x]Plant sunburn tolerance was rated on a scale of 1 to 5, with 1 being very poor, 3 being fair and acceptable, and 5 being excellent without showing any signs of leaf burns or resulted holes on leaf surfaces, taken in June, July, and August in 2005 and 2006.

The suitability for container forcing was evaluated by forcing tubers in 11.4-cm containers. No. 1 tubers of 'UF-85-5', 'Cranberry Star', 'Marie Moir', and 'Miss Muffet' were planted either intact or de-eyed in a peat/vermiculite mix (VerGro Container Mix A, Verlite, Tampa, Fla.) on Mar. 26, 2007. The study was conducted in a greenhouse with 45% light exclusion during the summer in Wimauma, Fla. Average daily temperatures ranged from a low of 16° C. at night to 29° C. during the day throughout the experiment. Potted plants were arranged on metal benches in the greenhouse in 10 randomized complete blocks. Plant height, number of leaves, and foliar characteristics were recorded 8 weeks after planting.

'UF-85-5' sprouted in 30 days (intact) or 32 days (de-eyed) after planting, similar to 'Miss Muffet' and 'Cranberry Star', but 4-9 days earlier than 'Marie Moir' (Table 3). Container-grown 'UF-85-5' was 19-22 cm tall regardless of tuber treatment (intact or de-eyed), similar to 'Marie Moir' and 'Cranberry Star', but significantly taller (5-8 cm) than 'Miss Muffet'. 'UF-85-5' produced 12 leaves on intact plants 8 weeks after planting and 21 leaves on de-eyed plants, similar to 'Miss Muffet', but significantly more than 'Marie Moir' or 'Cranberry Star'. Leaves of 'UF-85-5' were significantly smaller than those of 'Marie Moir', especially when tubers were planted intact: ~8 cm shorter and ~6 cm narrower. When tubers were de-eyed, leaf size differences became smaller and might be still significant. With numerous medium-sized leaves, 'UF-85-5' produced pot plants of much higher quality ratings (3.4-4.4) than 'Marie Moir' (1.9-2.4), and similar to 'Cranberry Star' and 'Miss Muffet', which are known for their superior pot habits. Tuber de-eyeing improved the plant quality of 'UF-85-5'.

TABLE 3

Plant performance for *Caladium* cultivars grown from No. 1 tubers in 11.4-cm containers in a 45% shaded glasshouse, Wimauma, Florida. Values represent the means of 10 plants produced from intact or de-eyed No. 1 (3.8-6.4 cm in diameter) tubers planted individually per container. Data were taken 8 weeks after planting.

| | Days to sprout[z] | | Plant height (cm) | | Leaves (no.) | |
|---|---|---|---|---|---|---|
| Cultivar | Intact | De-eye | Intact | De-eye | Intact | De-eye |
| 'UF-85-5' | 29.9 | 32.4 | 22.4 | 19.1 | 12.4 | 21.2 |
| 'Cranberry Star' | 31.9 | 34.3 | 22.5 | 25.5 | 7.0 | 12.1 |
| 'Marie Moir' | 34.1 | 41.2 | 23.4 | 19.6 | 4.9 | 6.8 |
| 'Miss Muffet' | 25.6 | 30.4 | 14.8 | 14.6 | 10.4 | 17.7 |

| | Leaf length (cm) | | Leaf width (cm) | | Quality rating | |
|---|---|---|---|---|---|---|
| Cultivar | Intact | De-eye | Intact | De-eye | Intact | De-eye |
| 'UF-85-5' | 20.6 | 16.6 | 13.9 | 10.2 | 3.4 | 4.4 |
| 'Cranberry Star' | 23.2 | 21.8 | 14.9 | 13.4 | 3.8 | 4.7 |
| 'Marie Moir' | 29.1 | 18.6 | 20.4 | 12.1 | 1.9 | 2.4 |
| 'Miss Muffet' | 19.1 | 14.7 | 12.1 | 8.2 | 3.3 | 4.1 |

[z]Number of days from planting to the first unfurled leaf.

What is claimed is:

1. A new and distinct cultivar of *Caladium* plant as shown and described herein.

* * * * *